United States Patent [19]

Bream

[11] 4,160,766
[45] Jul. 10, 1979

[54] AMINO CONTAINING BENZAZEPINES

[75] Inventor: John B. Bream, Berne, Switzerland

[73] Assignee: Sandoz Ltd., Basel, Switzerland

[21] Appl. No.: 906,838

[22] Filed: May 17, 1978

[30] Foreign Application Priority Data

May 23, 1977 [GB] United Kingdom ............... 21619/77

[51] Int. Cl.² .................. C07D 223/16; A61K 31/55; C07D 413/04
[52] U.S. Cl. ......................... 260/243.3; 260/239 BB; 260/244.4; 260/326.5 CA; 260/326.5 SF; 260/326.81; 260/340.5 R; 424/244; 424/248.52; 424/248.57; 424/248.58; 424/250; 424/267; 424/274; 424/282
[58] Field of Search ....................... 544/111, 359, 378; 260/239 BB, 293.58, 293.59, 326.5 CA, 326.5 SF, 326.81, 340.5 R, 243.3

[56] References Cited
U.S. PATENT DOCUMENTS

| | | | |
|---|---|---|---|
| 3,205,222 | 9/1965 | Johnson et al. | 260/239 BB |
| 3,321,466 | 5/1967 | Johnson et al. | 260/239 BB |

Primary Examiner—Natalie Trousof
Assistant Examiner—R. W. Ramsuer
Attorney, Agent, or Firm—Gerald D. Sharkin; Richard E. Vila; Joseph J. Borovian

[57] ABSTRACT

Compounds of formula I,

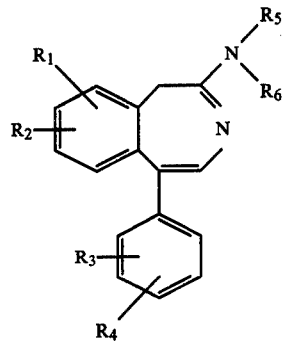

wherein either
 $R_1$ is hydrogen, halogen, trifluoromethyl or lower alkyl or alkoxy, and
 $R_2$ is hydrogen or lower alkoxy, or
 $R_1$ and $R_2$ together are methylenedioxy,
 $R_3$ is hydrogen, halogen, trifluoromethyl, lower alkyl or alkoxy or alkylsulphonyl,
 $R_4$ is hydrogen, halogen, lower alkyl or alkoxy, and
either
 (i)
 $R_5$ is hydrogen, lower alkyl or hydroxyalkyl, lower alkyl mono-substituted by cycloalkyl of 3 to 6 carbon atoms, cycloalkyl of 3 to 6 carbon atoms, lower alkenyl or alkynyl, wherein the multiple bond is in other than the $\alpha,\beta$-position, or phenylalkyl of 7 to 10 carbon atoms, and
 $R_6$ is hydrogen, lower alkyl or hydroxyalkyl, or
 (ii)
 $R_5$ and $R_6$ together with the nitrogen atom to which they are bound are 1-piperidinyl, 1-pyrrolidinyl, 1-morpholinyl, 1-piperazinyl or 1-(4-lower alkyl)-piperazinyl are useful as anti-aggressives and anti-depressives.

19 Claims, No Drawings

AMINO CONTAINING BENZAZEPINES

IMPROVEMENTS IN OR RELATING TO ORGANIC COMPOUNDS

The present invention relates to 5-phenyl-1H-3-benzazepine derivatives.

The present invention provides compounds of formula I,

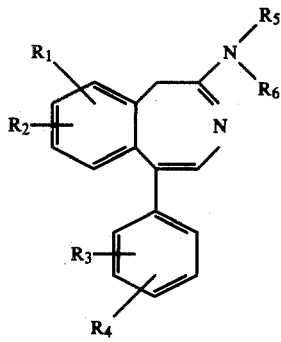

wherein either
  $R_1$ is hydrogen, halogen, trifluoromethyl or lower alkyl or alkoxy, and
  $R_2$ is hydrogen or lower alkoxy, or
  $R_1$ and $R_2$ together are methylenedioxy,
  $R_3$ is hydrogen, halogen, trifluoromethyl, or lower alkyl or alkoxy or alkylsulphonyl,
  $R_4$ is hydrogen, halogen, or lower alkyl or alkoxy, and
either
  (i)
    $R_5$ is hydrogen, lower alkyl or hydroxyalkyl, lower alkyl mono-substituted by cycloalkyl of 3 to 6 carbon atoms, cycloalkyl of 3 to 6 carbon atoms, lower alkenyl or alkynyl, wherein the multiple bond is in other than the $\alpha,\beta$-position, or phenylalkyl of 7 to 10 carbon atoms, and
    $R_6$ is hydrogen, lower alkyl or hydroxyalkyl, or
  (ii)
    $R_5$ and $R_6$ together with the nitrogen atom to which they are bound are 1-piperidinyl, 1-pyrrolidinyl, 1-morpholinyl, 1-piperazinyl or 1-(4-lower alkyl)-piperazinyl.

When $R_1$, $R_3$ and/or $R_4$ is halogen, this preferably refers to bromine and especially fluorine or chlorine. $R_1$ is conveniently halogen or especially hydrogen. $R_1$ is conveniently in the 7 or 8 position. $R_2$ is conveniently hydrogen. $R_3$ is conveniently in the 4-position and is preferably halogen or especially trifluoromethyl. $R_4$ is preferably hydrogen.

Lower alkyl or alkoxy or alkylsulphonyl has 1 to 4 carbon atoms, especially 1 carbon atom. Lower alkenyl or alkynyl preferably refers to radicals of 3 to 5 carbon atoms.

Lower hydroxyalkyl preferably refers to radicals of 1 to 4 carbon atoms, especially 2 or 3 carbon atoms. Preferably the hydroxy group is attached to a carbon atom other than the carbon atom adjacent to the nitrogen atom.

$R_6$ is conveniently alkyl or hydrogen.

The present invention provides a process for the production of a compound of formula I comprising
  (a) for the production of a compound of formula I, as defined above, wherein at least one of $R_5$ and $R_6$ are other than hydrogen, reacting a compound of formula Ia,

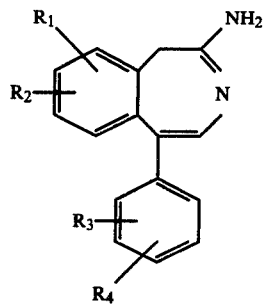

wherein $R_1$, $R_2$, $R_3$ and $R_4$ are as defined above, with a compound of formula II,

wherein at least one of $R_5$ and $R_6$ are other than hydrogen, or
  (b) for the production of a compound of formula Ia, as defined above, selectively reducing a compound of formula III,

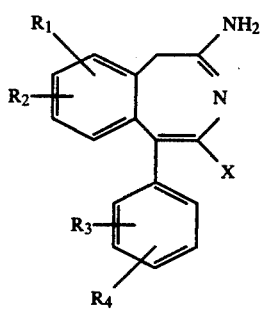

wherein $R_1$, $R_2$, $R_3$ and $R_4$ are as defined above, and X is bromine or iodine.

Process (a) may be effected in conventional manner for such transamination reactions.

The reaction is preferably carried out in solution. A suitable solvent is an alcohol such as ethanol. The reaction may be effected at temperatures ranging from room temperature to the reflux temperature of the solution, preferably from 30° to 50° C.

Process (b) may be effected in any conventional manner for the selective reduction of the halogen atom in a 4-halo-2-amino-1H-3-benzazepine.

The reaction may be carried out in solution. A suitable reducing agent is zinc dust in glacial acetic acid. An alcohol, e.g. methanol, may be used as co-solvent. The reaction is preferably carried out at temperatures ranging from 20° to 50° C. Conventional catalytic hydrogenation processes using, for example platinum or palladium-on-carbon catalysts, may alternatively be used.

X is preferably bromine.

Compounds of formula III may be obtained by reacting a compound of formula IV,

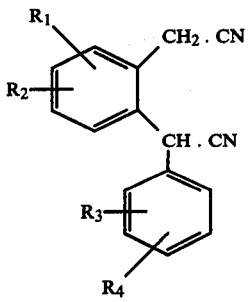

wherein $R_1$, $R_2$, $R_3$ and $R_4$ are as defined above, with a compound of formula V,

HX    V wherein X is as defined above, under anhydrous conditions, in conventional manner.

The compounds of formula IV may be obtained from the corresponding dibromo compounds by nucleophilic substitution with cyanide in conventional manner.

Free base forms of the compounds of formula I may be converted into acid addition salt forms in conventional manner and vice versa. Suitable acids are hydrochloric acid, hydrobromic acid, napthalene-1,5-disulphonic acid, oxalic acid, maleic acid and methane sulphonic acid.

Insofar as the production of starting materials is not particularly described these compounds are known and may be produced in known manner or in analogous manner to the processes described herein e.g. in the Examples or to known processes.

In the following Examples the temperatures given are in degrees Centigrade and are uncorrected.

In the Table the following abbreviations are used:
(1) decomposition
(2) hydrochloride salt
(3) monohydrate
(4) dihydrochloride salt
(5) monohydrochloride, 0.25 $H_2O$ salt
(6) hydrobromide salt
(7) monohydrochloride, 0.5 $H_2O$ salt
(8) demi-naphthalene-1,5-disulphonate salt
(9) hydrogen oxalate-monohydrate

EXAMPLE 1

7-Chloro-2-methylamino-5-phenyl-1H-3-benzazepine [process (a)]

2-Amino-7-chloro-5-phenyl-1H-3-benzazepine hydrochloride (8 g; 0.027 mole) [see Example (e)] in 33% w/w methylamine in ethanol (100 ml) was maintained at 40° for 3 days. The solution was then evaporated to dryness and the residual amine was azeotropically removed with toluene. The residue was treated with dry acetone, acidified with a few drops of ethanolic hydrogen chloride, filtered, and washed with acetone to give the title compound as the hydrochloride. Crystallisation of this hydrochloride from absolute ethanol gave a fine white granular powder; m.p. 318°–320°.

EXAMPLE 2

2-Amino-5-(4-trifluoromethylphenyl)-1H-3-benzazepine [process (b)]

A suspension of 38.1 g (0.1 mole) of 4-bromo-2-amino-5-(4-trifluoromethylphenyl)-1H-3-benzazepine and 1.8 g of 10% palladium on carbon in 1 liter methanol was shaken in a hydrogen atmosphere until 1 mole of hydrogen had been absorbed (ca. 4 hours). The catalyst was filtered off and the filtrate was evaporated under a vacuum. The residue was triturated with 200 ml of ether and filtered to give the hydrobromide of the title compound, m.p. 271°–289° (dec.). The above compound was converted into the free base form in conventional manner to give crystals of the title compound in free base form, which was recrystallised from ether/hexane; m.p. 167°–170°.

The free base form was also converted into the methanesulphonate; m.p. 234°–237°.

4-bromo-2-amino-5-(4-trifluoromethylphenyl)-1H-3-benzazepine used as starting material was obtained as follows:

(a) α-(4-Trifluoromethylphenyl)-o-xylyl dicyanide 37.4 g dried, finely powdered sodium cyanide was added over 5 minutes to a stirred solution of 155.8 g of α-(4-trifluoromethylphenyl)-o-xylyl dibromide in 1.5 liters dry dimethylformamide precooled to −10°. During the next 15 minutes the temperature of the mixture rose to about +4° and stirring was continued for 2.5 hours without external cooling. The reaction mixture was poured into 6 liters of water and the product was extracted first with toluene, then with ether. The combined toluene/ether layers were washed 4 times with 250 ml water, dried and evaporated. The residual oil was dissolved in diisopropyl ether. The solution was diluted with hexane until it just became cloudy and 20 ml diisopropyl ether were added to give a clear solution, which cooled and stirred overnight, gave the title compound, m.p. 80°–81°.

(b) 4-Bromo-2-amino-5-(4-trifluoromethylphenyl)-1H-3-benzazepine 90 ml of a 30–33% solution of hydrogen bromide in acetic acid was added dropwise to a stirred solution of 60.1 g of product (a) in 300 ml glacial acetic acid at room temperature over one hour. The resultant suspension was stirred over-night. The resultant crystals of the heading compound in hydrobromide form were filtered off and washed with ca. 225 ml ethyl acetate. Further crystals can be obtained by evaporating the filtrate and triturating the residual oil with ethyl acetate and adding ether. The resulting 4-bromo-2-amino-5-(4-trifluoromethylphenyl)-1H-benzazepine hydrobromide was converted in conventional manner into the free base form, m.p. 227°–229°.

In analogous manner to that described in Example 1 there are obtained the following compounds of formula I wherein:

| EXAMPLE No. | $R_1$ | $R_2$ | $R_3$ | $R_4$ | $NR_5R_6$ | m.p. |
|---|---|---|---|---|---|---|
| (3) | H | H | H | H | —NHCH$_3$ | 243°–246°(2) |
| (4) | H | H | 4-Cl | H | —NHCH$_3$ | 197°–202°/225° (HCl . CH$_3$OH salt) |
| (5) | H | H | H | H | —N(CH$_3$)$_2$ | 284°–285°(2)(3) |

-continued

| | | | | | | |
|---|---|---|---|---|---|---|
| (6) | H | H | H | H | —N(piperazinyl)N—CH₃ | 301°–304°[4] |
| (7) | 7-Cl | H | H | H | —N(CH₃)₂ | 155°–158° |
| (8) | H | H | H | H | —NH(CH₂)₂·OH | 219°–222° |
| (9) | H | H | H | H | —NH(CH₂)₃·OH | 143°–144° |
| (10) | 7-Cl | H | H | H | —N(piperidinyl)NCH₃ | 285°–287°[2] |
| (11) | 7-Cl | H | H | H | —NH(CH₂)₂·OH | 150°–151° |
| (12) | 7-Cl | H | H | H | —NH(CH₂)₃·OH | 192°–193° |
| (13) | 7-Cl | H | H | H | —NH(n)C₃H₇ | 266°–267°[2] |
| (14) | 7-Cl | H | H | H | —N(pyrrolidinyl) | 303°–304°[1][5] |
| (15) | 7-Cl | H | H | H | —N(morpholinyl)O | 309°–310°[2] |
| (16) | 7-Cl | H | H | H | —NH(CH₂)₂C₆H₅ | 120°–125°[2][3] |
| (17) | 7-Cl | H | H | H | NH·CH₂·C₆H₅ | 168°–176°[2] |
| (18) | H | H | 4-Cl | H | —N(CH₃)₂ | 260°–272°[1][2] |
| (19) | H | H | 4-Cl | H | —NH(CH₂)₂C₆H₅ | 248°[1][2] |
| (20) | H | H | 4-CF₃ | H | —N(CH₃)₂ | 136°–138° |
| (21) | 7-Cl | H | 4-Cl | H | —N(CH₃)₂ | 215°–216° |
| (22) | 8-Cl | H | H | H | —NH(CH₂)₂OH | 172°–173° |
| (23) | H | H | 3-Cl | 4-Cl | —N(CH₃)₂ | 146°–149° |
| (24) | H | H | 4-Cl | H | —N(C₂H₅)₂ | 147°–150° |
| (25) | 8-Cl | H | 4-Cl | H | —N(CH₃)₂ | 201°–202° |
| (26) | 8-Cl | H | H | H | —N(CH₃)₂ | 159°–160° |
| (27) | H | H | 4-Cl | H | —N(pyrrolidinyl) | 175°–178° |
| (28) | H | H | 4-F | H | —N(CH₃)₂ | 140°–141° |
| (29) | H | H | 4-Cl | H | —N(CH₃)·CH₂·CH₂·C₆H₅ | 213°–228°[2] |
| (30) | H | H | 4-Cl | H | —N(piperazinyl)N—CH₃ | 148°–149° |
| (31) | H | H | 4-Cl | H | —N(CH₃)CH₂—CH=CH₂ | 109°–112° |
| (32) | H | H | 4-Cl | H | —N(CH₃)CH₂—C≡CH | >290°[7] |
| (33) | H | H | 4-Cl | H | —NH(CH₂)₃OH | 144°–146°[2] |
| (34) | H | H | 4-Cl | H | —NH(CH₂)₂OH | 229°–238°[1][2] |
| (35) | H | H | 4-Cl | H | —N(CH₃)·C₂H₅ | 158°–162° |
| (36) | H | H | 4-Cl | H | —N(piperidinyl) | 154°–155° |
| (37) | H | H | 3-CF₃ | H | —N(CH₃)₂ | 282°–288°[8] |
| (38) | H | H | 4-CF₃ | H | —NH(CH₂)₂C₆H₅ | 250°–259°[2] |
| (39) | H | H | 4-CF₃ | H | —NHC(CH₃)₃ | 275°–278°[2][1] |
| (40) | H | H | 4-CF₃ | H | —N(CH₃)CH₂CH=CH₂ | 87°–91° |
| (41) | H | H | 4-CF₃ | H | —NHCH₃ | 287°–298°[2][1] |
| (42) | H | H | 4-CF₃ | H | —N(CH₃)(n)-C₃H₇ | 123°–125° |
| (43) | H | H | 4-CF₃ | H | —NH-cyclohexyl | 138°–141° |
| (44) | H | H | 4-CF₃ | H | —NHCH(CH₃)₂ | 198°–205°[2] |
| (45) | H | H | 4-CF₃ | H | —NHCH₂—CH=CH₂ | 206°–212°[2] |
| (46) | H | H | 4-CF₃ | H | —NHCH₂-cyclopropyl | 228°–234°[2][1] |
| (47) | H | H | 4-CF₃ | H | —NH(CH₂)₂OH | 234°–237°[2][1] |
| (48) | H | H | 4-CF₃ | H | —N(CH₃)CH₂C≡CH | 228°[9][1] |

| EXAMPLE No. | R₁ | R₂ | R₃ | R₄ | NR₅R₆ |
|---|---|---|---|---|---|
| (49) | 6-C₂H₅ | 8-OC₂H₅ | 3-OC₂H₅ | 4-OC₂H₅ | N[(CH₂)₂—OH]₂ |
| (50) | 6-OC₂H₅ | 8-OC₂H₅ | 3-OC₂H₅ | 4-OC₂H₅ | —N(piperazinyl)NH |

-continued

| | | | | |
|---|---|---|---|---|
| (51) | 7,8-O—CH$_2$—O— | 3-OC$_2$H$_5$ | 4-OC$_2$H$_5$ | —N⟨ ⟩NH (piperazinyl) |
| (52) | 6-OC$_2$H$_5$ | 9-OC$_2$H$_5$ | 3-C$_2$H$_5$ | 4-C$_2$H$_5$ | —N⟨ ⟩NH (piperazinyl) |

In analogous manner to that described in Example 2 from the appropriate compound of formula III, wherein X is bromine, there are obtained the following compounds of formula Ia:

| EXAMPLE No. | R$_1$ | R$_2$ | R$_3$ | R$_4$ | m.p. |
|---|---|---|---|---|---|
| (a) | H | H | H | H | 227°–279°(2) |
| (b) | 7-Cl | H | 4-Cl | H | 264°–270°(1)(2) |
| (c) | H | H | 4-Cl | H | 218°–225° |
| (d) | 8-Cl | H | H | H | 273°–279°(1)(2) |
| (e) | 7-Cl | H | H | H | 284°–286°(2)(1) |
| (f) | H | H | 2-Cl | H | 269°–274°(1)(6) |
| (g) | 8-Cl | H | 4-Cl | H | 278°–283°(1)(2) |
| (h) | H | H | 3—Cl | H | 180°–182° |
| (i) | H | H | 4-CH$_3$ | H | 202°–208° |
| (j) | H | H | 4-F | H | 172°–180° |
| (k) | H | H | 3-Cl | 4-Cl | 214°–220° |
| (l) | H | H | 3-CF$_3$ | H | 195°–198°(2) |
| (m) | H | H | 2-CF$_3$ | H | 185°–192°(1) |
| (n) | 8-Cl | H | 4-CF$_3$ | H | 193°–197°(1) |
| (o) | 7-CF$_3$ | H | H | H | 180°–186° |
| (p) | H | H | 4-SO$_2$CH$_3$ | H | 244°(1) |

The compounds of formula I are useful because they possess pharmacological activity in animals. In particular, the compounds of formula I are useful as anti-aggressive agents, as indicated in the isolation induced aggression test in mice on oral administration of from 3 to 30 mg/kg animal body weight of the compounds, and a significant sedative effect in the climbing test with mice only at higher doses.

For the above-mentioned use the dosage will, of course, vary depending on the compound employed, mode of administration and therapy desired. However, in general, satisfactory results are obtained with a daily dosage of from 0.5 mg to about 30 mg per kg animal body weight, conveniently given in divided doses 2 to 4 times a day or in sustained release form. For the larger mammal, the total daily dosage is in the range from about 50 to about 500 mg, and dosage forms suitable for oral administration comprise from about 12 mg to about 250 mg of the compounds admixed with a solid or liquid pharmaceutical carrier or diluent.

Additionally, the compounds of formula I are useful as anti-depressant agents, as indicated by standard tests, e.g. an antagonism of tetrabenazine-induced ptosis and catalepsy in the rat on parenteral administration of from 10 to 50 mg/kg animal body weight of the compounds.

For the above-mentioned use the dosage will, of course, vary depending on the compound employed, mode of administration and therapy desired. However, in general, satisfactory results are obtained with a daily dosage of from 0.05 mg to about 50 mg per kg animal body weight, conveniently given in divided doses 2 to 4 times a day or in sustained release form. For the larger mammal, the total daily dosage is in the range from about 4 to about 200 mg, and dosage forms suitable for oral administration comprise from about 1 mg to about 100 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methanesulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions may be prepared by conventional techniques to be in conventional forms, for example, capsules or tablets.

In a first group of compounds R$_5$ is hydrogen.
In a second group of compounds R$_5$ is alkyl.
In a third group of compounds R$_5$ is cycloalkylalkyl.
In a fourth group of compounds R$_5$ is cycloalkyl.
In a fifth group of compounds R$_5$ is alkenyl.
In a sixth group of compounds R$_5$ is alkynyl.
In a seventh group of compounds R$_5$ is phenylalkyl.
In a eight group of compounds R$_5$ and R$_6$ together are 1-piperidinyl.
In a ninth group of compounds R$_5$ and R$_6$ together are 1-pyrrolidinyl.
In a tenth group of compounds R$_5$ and R$_6$ together are 1-morpholinyl.
In an eleventh group of compounds R$_5$ and R$_6$ together are 1-piperazinyl.
In a twelfth group of compounds R$_5$ and R$_6$ together are 1-(4-lower alkyl)-piperazinyl. The Example 2 compound is the most interesting compound, and the anti-aggressive activity is the preferred utility.

What we claim is:
1. A compound of formula I,

(structure of formula I shown with substituents R$_1$, R$_2$, R$_3$, R$_4$, R$_5$, R$_6$ and N atoms)

wherein either
R$_1$ is hydrogen, halogen, trifluoromethyl or lower alkyl or alkoxy, and
R$_2$ is hydrogen or lower alkoxy, or
R$_1$ and R$_2$ together are methylenedioxy, $R_3$ is hydrogen, halogen, trifluoromethyl, or lower alkyl or alkoxy or alkylsulphonyl, $R_4$ is hydrogen, halogen, or lower alkyl or alkoxy, and either (i)

$R_5$ is hydrogen, lower alkyl or hydroxyalkyl, lower alkyl mono-substituted by cycloalkyl of 3 to 6 carbon atoms, cycloalkyl of 3 to 6 carbon atoms, lower alkenyl or alkynyl, wherein the multiple bond is in other than the $\alpha,\beta$-position, or phenylalkyl of 7 to 10 carbon atoms, and $R_6$ is hydrogen, lower alkyl or hydroxyalkyl, or (ii)

$R_5$ and $R_6$ together with the nitrogen atom to which they are bound are 1-piperidinyl, 1-pyrrolidinyl, 1-morpholinyl, 1-piperazinyl or 1-(4-lower alkyl)-piperazinyl, in free base form or in pharmaceutically acceptable acid addition salt form.

2. A compound of claim 1, wherein $R_2$ is hydrogen.

3. A compound of claim 1, which is 2-amino-5-(4-trifluoromethylphenyl)-1H-3-benzazepine.

4. A compound of claim 2, which is 5-(4-chlorophenyl)-2-dimethylamino-1H-3-benzazepine.

5. A compound of claim 5, which is 2-dimethylamino-5-(4-trifluoromethylphenyl)-1H-3-benzazepine.

6. A compound of claim 2, which is 5-(4-chlorophenyl)-2-diethylamino-1H-3-benzazepine.

7. A compound of claim 2, which is 2-allylmethylamino-5-(4-chlorophenyl)-1H-3-benzazepine.

8. A compound of claim 2, which is 2-methylamino-5-(4-trifluoromethylphenyl)-1H-3-benzazepine.

9. A compound of claim 2, which is 2-methylpropylamino-5-(4-trifluoromethylphenyl)-1H-3-benzazepine.

10. A compound of claim 2, which is 2-isopropylamino-5-(4-trifluoromethylphenyl)-1H-3-benzazepine.

11. A compound of claim 2, which is 2-allylamino-5-(4-trifluoromethylphenyl)-1H-3-benzazepine.

12. A compound of claim 2, which is 2-(cyclopropylmethyl)-amino-5-(4-trifluoromethylphenyl)-1H-3-benzazepine.

13. A compound of claim 2, wherein $R_5$ and $R_6$ are both hydrogen.

14. A compound of claim 13, which is 2-amino-5-(4-chlorophenyl)-1H-3-benzazepine.

15. A compound of claim 13, which is 2-amino-8-chloro-5-phenyl-1H-3-benzazepine.

16. A compound of claim 13, which is 2-amino-7-chloro-5-phenyl-1H-3-benzazepine.

17. A compound of claim 13, which is 2-amino-8-chloro-5-(4-trifluoromethylphenyl)-1H-3-benzazepine.

18. A compound of claim 13, which is 2-amino-5-phenyl-7-trifluoromethyl-1H-3-benzazepine.

19. A compound of claim 13, which is 2-amino-5-(4-methylsulphonylphenyl)-1H-3-benzazepine.

* * * * *